United States Patent [19]

Rosenberg

[11] Patent Number: 4,472,139
[45] Date of Patent: Sep. 18, 1984

[54] INTRAORAL DENTAL APPLIANCE FOR CORRECTING CLASS II MALOCCLUSIONS ORTHOPEDICALLY

[76] Inventor: Farel A. Rosenberg, 10535 Wilshire Blvd. #1811, Los Angeles, Calif. 90024

[21] Appl. No.: 502,704
[22] Filed: Jun. 9, 1983
[51] Int. Cl.³ ............................................... A61C 7/00
[52] U.S. Cl. ..................................................... 433/19
[58] Field of Search ....................................... 433/19, 7

[56] References Cited

U.S. PATENT DOCUMENTS

| | | | |
|---|---|---|---|
| 3,618,214 | 11/1971 | Armstrong | 433/19 |
| 3,654,702 | 4/1972 | Kelly, Jr. | 433/19 |
| 3,798,773 | 3/1974 | Northcutt | 433/19 |
| 3,832,778 | 9/1974 | Wallshein | 433/7 |
| 4,382,783 | 5/1983 | Rosenberg | 433/19 |

OTHER PUBLICATIONS

E. Herbst "Rundshau" vol. 34, p. 1515, 1934.

*Primary Examiner*—Robert Peshock
*Attorney, Agent, or Firm*—Gilbert Kivenson

[57] ABSTRACT

An orthopedic appliance for correcting an abnormal, Class II malocclusion. In the latter the mandible and its teeth are posteriorly displaced resulting in improper biting and impaired physical appearance. An adjustable bar attached in each side of the mouth to upper and lower molars is used to join the upper and lower rows of teeth. The point of attachment to the lower row of teeth is somewhat forward of the corresponding point in the upper row so that the lower jaw is forced forward when the mouth is closed. In adolescents, and to some extent in adults, this produces permanent muscle changes of the lower jaw and its joint, bone remodeling and permanent correction of the occlusion to a normal Class I bite. The appliance uses no telescoping sections, is easily manufactured and is readily adjustable during installation and wearing.

5 Claims, 5 Drawing Figures

INTRAORAL DENTAL APPLIANCE FOR CORRECTING CLASS II MALOCCLUSIONS ORTHOPEDICALLY

BACKGROUND OF THE INVENTION

This invention relates to orthopedic appliances for the correction of Class II malocclusions in children and adults. In these malocclusions the upper row of teeth are found considerably ahead of the lower row.

This invention represents an extension of and improvement on the appliances taught in my U.S. Pat. No. 4,382,783. Although appliances made according to the latter patent are a considerable improvement on prior art, the use of telescoping sections has been found in practice to complicate manufacturing procedures. In addition, the provision of a single link as described in my previous patent makes for relatively large overall dimensions of the appliance and is therefore not suitable for the younger patient.

It is an objective of this invention to provide a design which is relatively easy to manufacture. It is another objective of this invention to provide the same functions as my previous appliance without the use of telescoping sections. It is yet a further objective to provide a smaller appliance which may be used for younger patients without sacrificing previously achieved features. The latter includes: (a) freedom of lateral and vertical movement while maintaining any orthopedically-adjusted front to back (sagital) jaw relationship, (b) compatability with conventional orthodontic treatment including the use of full banding, partial banding, or bonding to hold arch wire supports.

SUMMARY OF THE INVENTION

In this invention the upper and lower sets of teeth are movably connected by both a right and left or just a right or left bar of adjustable length. The bar is joined, by pivoted links at each of its ends, to anchor bands cemented to first molars or other suitable teeth. The bars and their linkages utilize the effort of closing the mouth to exert any desired amount of additional horizontal force on the lower jaw to push it into a corrected position with respect to the upper jaw. These forward, corrective forces are exerted automatically as long as the appliance remains installed in the mouth and increase to a maximum when full closure is reached. After the linkages are worn for a period of months and lengthened if necessary by adjusting of the bars, a permanent change in the positional relationship of the upper and lower sets of teeth can be achieved through an orthopedic forward movement of the lower jaw.

DESCRIPTION OF THE INVENTION

Figure 1:
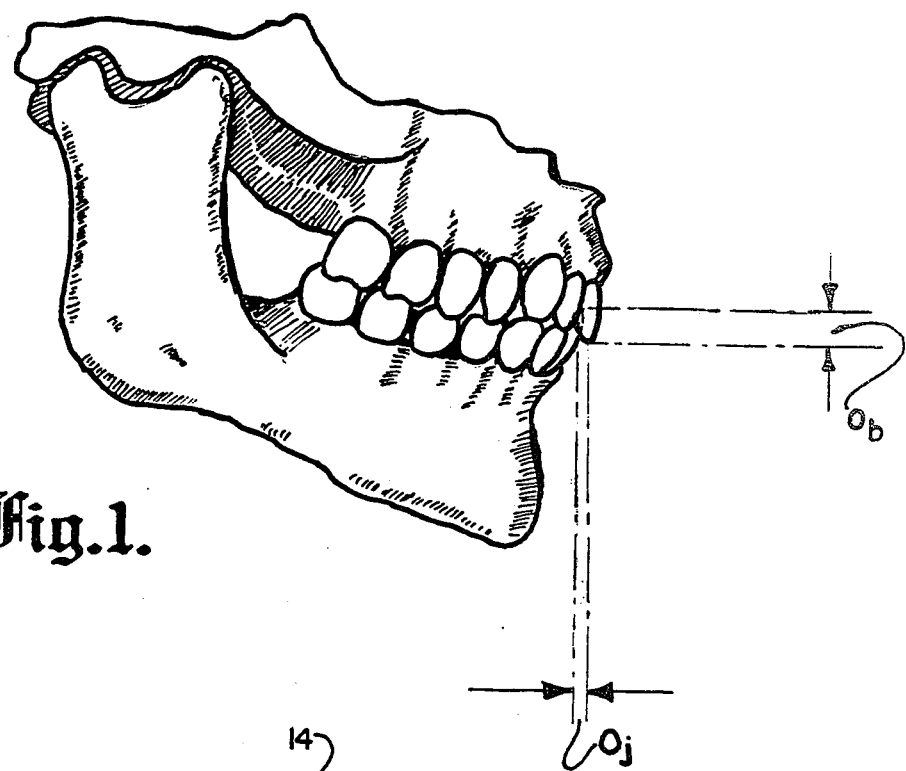
FIG. 1 is a right side view of one case of malocclusion.

FIG. 1, which illustrates an exaggerated form of Class II malocclusion, also shows the two common and undesirable conditions which exist under these circumstances. Because of retrusion of the mandible there is an exaggerated "overjet" $O_j$. This is accompanied by the second abnormal condition, the excessive "overbite" $O_b$. These abnormalities interfere with proper functioning of the teeth, and also detract from the person's appearance. It has been found that continuously forcing the mandible forward by the use of an orthopedic device for altering bone position for a period of months achieves an improved alignment between the upper and lower rows of teeth. With proper application of the device, and the simultaneous use of conventional orthodontic methods, it is possible to achieve a permanent correction of the malocclusion and an improved facial profile. The combined technique also eliminates extractions of teeth which might be necessary to achieve the same result if only orthodontic methods were utilized.

Figure 2:
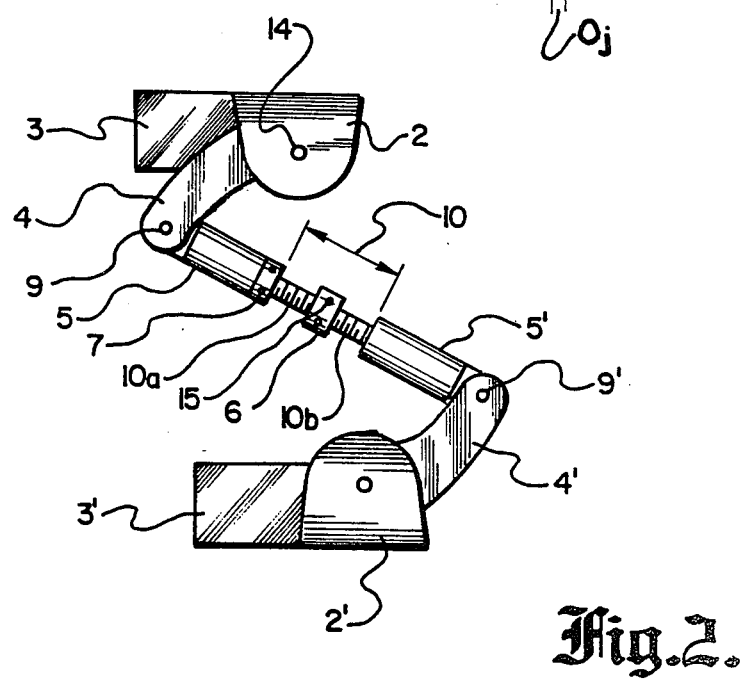
FIG. 2 is a side view of an appliance as made in accordance with the principles of the present invention. Two such appliances—a right and left—would usually be used in each application.

The general operation of the present invention will now be explained with reference to FIGS. 2, 3 and 4. A pair of internally threaded cylinders 5 and 5' in FIG. 2 are joined by the positioning screw 10. The threads within cylinder 5 and the upper portion of 10 (10a) are right handed while cylinder 5' and the lower portion 10b carry left handed threads. When the central hub 6 is turned by means of a pin inserted in one of its holes 15, the cylinders 5 and 5' are simultaneously brought together or simultaneously separated. The cylinders are each flattened at one end and attached by pins 9 and 9' to the links 4 and 4' respectively. The links are themselves pivoted at 14 and 14'. The link holders 2 and 2' are extended backwardly to form the lateral hinges 3 and 3' which are pivotably and medially mounted to open tubes horizontally attached to bands. The latter are cemented to the first molars or to teeth functioning as first molars. When the mouth is closing, FIG. 3, the links move into the link holders until no further motion in this mode is possible. Up to this point (position X in FIG. 3) the arc of closure of the lower jaw is unchanged from what it would be without the appliance. Further closure of the mouth results in a force which pushes the lower jaw further forward. This creates a new arc XN for the lower jaw instead of the arc XM which is followed as a result of the malocclusion. The amount that the lower jaw is forced forward is determined by the combined length of the cylinders 5 and 5' and the exposed portions 10a and 10b of the positioning screw. The latter is adjusted by turning the central hub 6 as was explained previously. A nut 7 is provided to lock the adjustment at any desired point. Increasing of the separation of the cylinders by the orthodontist produces an immediate or gradual repositioning of the lower jaw (a protrusion). The corrected position of the mandible on closure after some months of treatment is shown in FIG. 4.

Figure 3:
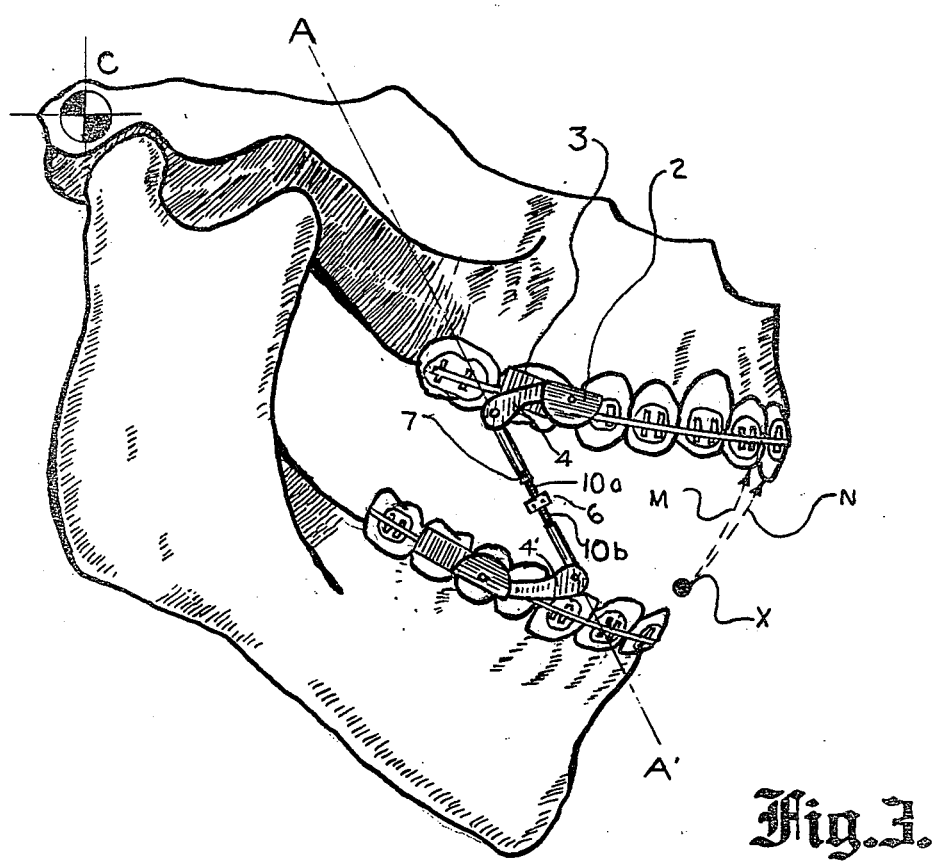
FIG. 3 is a right side view of the appliance of FIG. 2 installed in the mouth. The invention is attached to tubes welded to molar bands, which are in turn secured by cementing to upper and lower molars or to teeth functioning as first molars.
Figure 4:
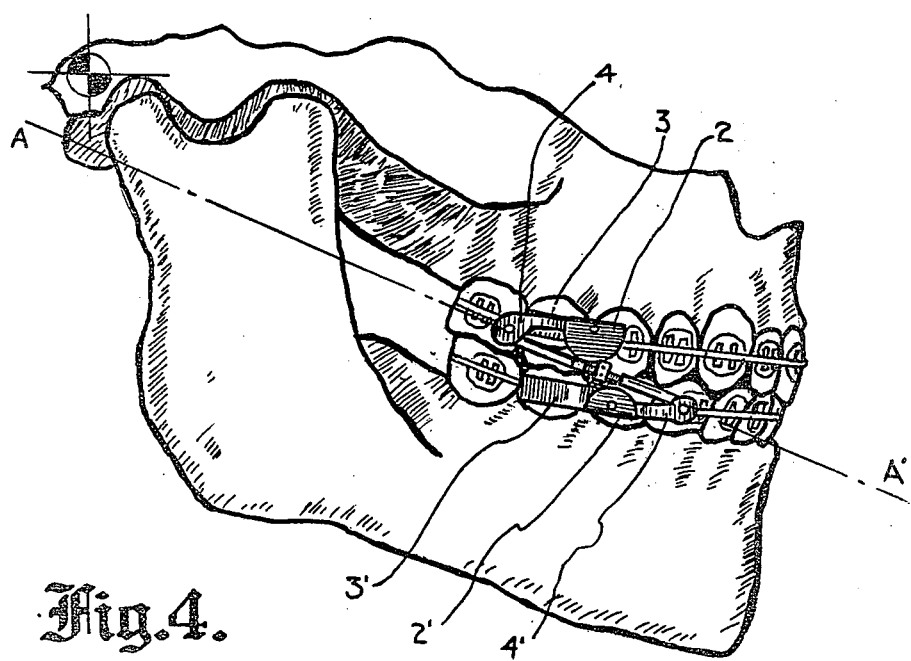
FIG. 4 is the same as FIG. 3 but with the mouth closed and showing the mandibular teeth in their now corrected forward position, i.e., the normal Class I occlusion achieved by the invention.

The axis of the cylinders and positioning screw assembly is shown by A-A' in FIGS. 3 and 4. With the mouth open, A-A' extends above the mandibular condyle (the hinging structure C) of the lower jaw. When the mouth is closed, A-A' extends somewhat below this joint so that a toggling or mild locking action is obtained. The presence or absence of toggling can be pre-determined by variation in length of the links 4 and 4'. In some cases toggling is desirable because the lower jaw would be held in the position of maximum correction during relaxed periods such as when the patient is asleep. In other cases toggling might be annoying during eating. The orthodontist would determine from individual patient characteristics whether toggling was desirable and size the appliance accordingly.

Figure 5:
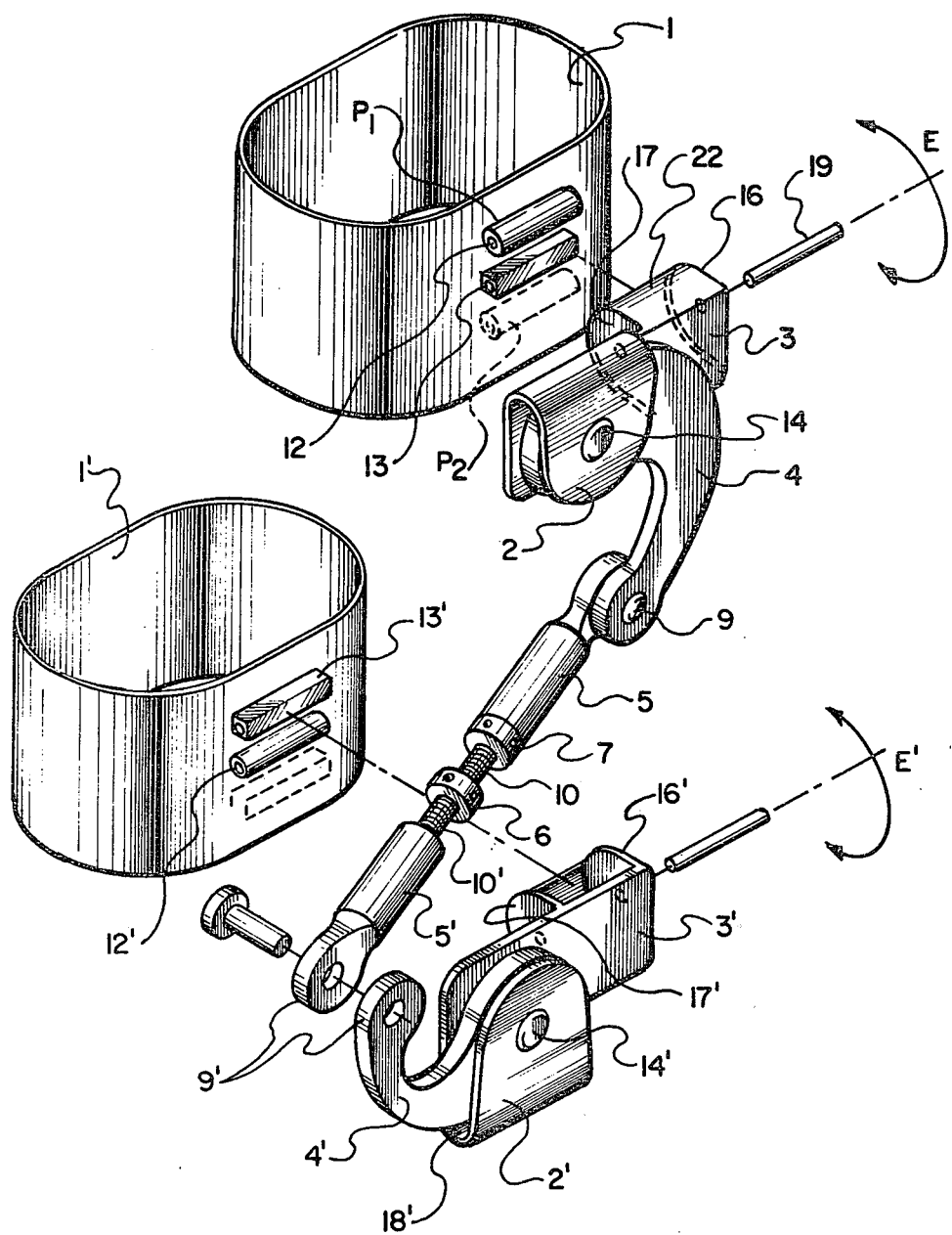
FIG. 5 is an exploded view of a complete appliance for the left side of the mouth made in accordance with the principles of the invention.

Further details of the invention will now be discussed with reference to FIG. 5 in which 1 and 1' represent a standard type of orthodontic band which is commonly used in the straightening of teeth. To each upper and lower band 1 and 1' is welded a rectangular archwire tube section 13 and 13' and a section of circular tube 12 and 12'. The tube 12 can be positioned at $P_1$ or $P_2$ to accommodate individual variations in tooth size. In conventional orthodontic procedure the rectangular tubes hold rectangular or circular archwires while the circular tubes serve for externally mounted headgear. In orthodontic practice the archwires are extended from tooth to tooth in each dental arch to exert forces on individual teeth. In the use of the present invention, four dual-purpose cemented bands are required—one band for each first molar. An appliance is mounted between each upper and lower pair of these bands. In some cases (e.g. an asymmetric mandible) an appliance may be required on only one side of the mouth. Concurrent placement and use of other bands in conventional orthodontic treatment is not disturbed.

The upper and lower link holders 2 and 2' contain the openings 18 and 18' to accommodate the links 4 and 4'. The link holders extend backwardly to form the hinges 3 and 3'. The outer hinge ears 16 and 16' are formed by bending the ends of 3 and 3' inwardly. The inner hinge ears 17 and 17' may be attached by welding. The hinges are rotatably mounted to the horizontally placed circular tubes 12 and 12' by the fasteners 19 and 19'. This mounting, along with intentionally-provided play in the pin joints 9,9', 14 and 14' allows movement in the directions E and E' and thus permits some lateral movement of the lower jaw, an important feature in preserving patient comfort. Metal stops 22 and 22' are attached between hinge ears 16 and 17 and 16' and 17' respectively to limit motion in the E and E' directions. These stops prevent contact of parts of the linkage with oral tissues. The hinge ears 16 and 17 and 16' and 17' are sufficiently long to allow movement of the appliance without interference with the rectangular tubes 13 and 13' and the arch wires entering and exiting them. As was mentioned earlier, this is an important feature of the invention because it permits the simultaneous continuance of conventional orthodontic procedures while the orthopedic correction of the jaw is in progress. The presence of a full set of bands in the mouth is in fact an advantage because the lingual surface of the metal bands can be used for additional stabilization of the invention. This is done by attaching additional tubes to the tongue side of these bands and using more wires to brace the first molars to adjacent teeth. This extra stabilization and anchoring can limit unfavorable tooth movement which may occur in some cases as a reaction to forcing the lower jaw forward.

I claim:

1. An intraoral, two-part dental appliance to improve orthopedically a retrusive mandible in the correction of Class II dental malocclusions, one part of which is mounted in the right side and the other in the left side of the mouth, each part comprising:
    (a) an upper anchoring means secured preferably to any upper tooth functioning as a first molar;
    (b) a lower anchoring means secured preferably to any teeth functioning as a first molar;
    (c) an upper link holder pivotally attached to said upper anchoring means;
    (d) a lower link holder pivotally attached to said lower anchoring means;
    (e) an upper link so pinned within said upper link holder as to permit limited rotary motion from front to back within a prescribed arc;
    (g) an upper cylinder internally and partially threaded, and pivotally joined at the end away from the thread to the free end of the upper link;
    (h) a lower cylinder internally and partially threaded in an opposite handedness to the internal thread of the upper cylinder and pivotally joined at the end away from the thread to the free end of the lower link;
    (i) a positioning screw having right and left handed threads on its opposite ends, having a cross drilled central hub in its center and a locking means on one of its threads, said positioning screw being threaded into the upper and lower cylinders to provide a continuous and adjustable assembly between the upper and lower rows of teeth on each side of the mouth; whereby closure of the mouth from a wide open position first causes rotation of the links into their respective link holders until their limit of front to back rotary motion is reached, then said closure is resolved into a forward and downward movement of the lower jaw with respect to the jaw joint and upper teeth, thus aligning the lower row of teeth with the upper row to a corrected occlusal relationship.

2. An intraoral two-part dental appliance as described in claim 1 in which said upper and lower anchoring means are metal bands to which horizontal tube sections are rigidly joined to permit pivotal attachment of the said upper and lower link holders, said bands being cemented preferably to teeth functioning as upper and lower first molars.

3. An intraoral, two-part appliance as described in claim 1 in which each continuous and adjustable assembly can be varied in length, after the appliance is installed, by the insertion of a pin into the cross-drilled central hubs and turning the positioning screws, the variation in length serving to equalize the forward and downward forces applied on each side of the lower jaw when the mouth is in closed position and to advance the jaw travel as treatment progresses.

4. An intraoral dental appliance as described in claim 1 in which said locking means is a nut of a handedness matching the thread on which it is placed and which is capable of being tightened against its adjacent cylinder.

5. An intraoral dental appliance as described in claim 1 in which the operating axes of the various pivoting arrangements as well as their looseness of fit permit the user to have lateral freedom of jaw movement while maintaining a forward and downward positioning force on the mandible at mouth closure.

* * * * *